United States Patent [19]

King

[11] Patent Number: 5,334,941
[45] Date of Patent: Aug. 2, 1994

[54] MICROWAVE REFLECTION RESONATOR SENSORS

[75] Inventor: Ray J. King, Pleasanton, Calif.

[73] Assignee: KDC Technology Corp., Livermore, Calif.

[21] Appl. No.: 944,526

[22] Filed: Sep. 14, 1992

[51] Int. Cl.$^5$ .............................................. H01P 3/08
[52] U.S. Cl. ................... 324/637; 324/638; 324/642; 333/230
[58] Field of Search ............... 324/633, 637, 638, 639, 324/642, 643, 707, 708; 333/26, 227, 230; 343/767, 820

[56] References Cited

U.S. PATENT DOCUMENTS

| | | |
|---|---|---|
| 3,510,764 | 5/1970 | Heath . |
| 3,760,304 | 9/1973 | Cohn .................... 333/209 |
| 3,942,107 | 3/1976 | Gerhard . |
| 4,123,730 | 10/1978 | Fikart ..................... 333/26 |
| 4,780,661 | 10/1988 | Bolomey et al. ............ 324/638 |
| 4,829,233 | 5/1989 | Flemming et al. ........... 324/633 |
| 4,865,370 | 9/1989 | Flemming et al. ........... 324/639 |
| 5,187,443 | 2/1993 | Bereskin .................. 324/639 |
| 5,227,730 | 7/1993 | King et al. ............... 324/632 |

OTHER PUBLICATIONS

Ginzton, R. L. *Microwave Measurements,* McGraw Hill, 1957, p. 437.
Pozar, D. M., "Microstrip Antenna Coupled to a Microstrip Line", Electronics Letters, 21, 17 Jan., 1985, pp. 49–50.
Pozar, D. M. and R. W. Jackson, "An Aperture Coupled Microstrip Antenna with a Proximity Feed on a Perpendicular Substrate," IEEE Trans. on Antennas and Propagation, AP-35(6), Jun. 1987, pp. 728–731.
Buck, A. C., and D. M. Pozar, "Aperture-Coupled Microstrip Antenna with a Perpendicular Feed," Electronics Letters, 22(3), Jan. 1986, pp. 125–126.
Pozar, D. M., "An Update on Microstrip Antenna Theory and Design Including Some Novel Feeding Techniques," IEEE AP-Society Newsletter, Oct., 1986, pp. 5–9.

*Primary Examiner*—Kenneth A. Wieder
*Assistant Examiner*—Christopher Tobin
*Attorney, Agent, or Firm*—Henry P. Sartorio

[57] ABSTRACT

A highly sensitive, direct-contact, in situ sensor for nondestructively measuring or monitoring the complex dielectric and conductive properties of solids, liquids, or gasses at microwave frequencies. A metal microstrip dipole resonator (11) is etched on the surface of a dielectric substrate (12) which is bonded to a copper ground plane (14). The dipole resonator is electromagnetically driven by mutual inductive coupling to a short nonresonant feed slot (13) formed in the ground plane (14). The slot (13) is driven by a coaxial feed line (7) or a microstrip feed line (16) extending from a swept microwave frequency source (2) which excites the incident wave (17). Alternatively, the metal resonator is omitted and the length of the slot (15) is increased so that it becomes the resonator. In use, the sensor is placed in close physical contact with the test material (9) having complex dielectric constant $\epsilon^* (=\epsilon'-j\epsilon'')$ or conductivity $\sigma$. As the frequency of the microwave source (2) is swept, a sharp dip in the reflected wave (18) occurs at the resonant frequency, provided that the coaxial feed line (7) or microstrip feed line (16) is nearly critically coupled to the sensor input. Measurement of the resonant frequency and input coupling factor determines small changes in $\epsilon'$, $\epsilon''$ and $\sigma$ with great resolution. To diminish the electromagnetic coupling between the resonator (11) and the test material (9), and to protect the resonator (11) from damage and wear, a superstrate (26) may be added.

29 Claims, 4 Drawing Sheets

MICROWAVE REFLECTION RESONATOR SENSORS

GOVERNMENT RIGHTS

This invention was made with Government support under Contract 50-DKNA-8-00168 awarded by the U.S. Department of Commerce/NOAA, and Contract N68335-89-C-0455, awarded by the Naval Air Engineering Center. The Government has certain rights in the invention.

BACKGROUND

1. Field of Invention

This invention relates to the use of microwave reflection resonator sensors for measuring or monitoring the complex dielectric or conductive properties of materials in situ.

2. Discussion of Prior Art

Microstrip resonator sensors are effective devices for measuring the complex dielectric constant $\epsilon^*$ ($=\epsilon'-j\epsilon''$) of materials at microwave frequencies as disclosed by Flemming U.S. Pat. No. 4,865,370), by Heath U.S. Pat. No. 3,510,764) and by Gerhard U.S. Pat. No. 3,942,107). Flemming describes a method in which a microstrip resonator is mounted on a copper-backed dielectric substrate. The resonator is weakly capacitively coupled to a microwave feed source and to a microwave detector so that the resonator Q-factor is not affected by the impedances of the source or the detector. When the test dielectric is placed near the resonator, the electromagnetic fields near the resonator are coupled to the test dielectric so as to affect the resonator's resonant frequency and Q-factor as measured by a detector for transmission between the separate sensor input and output ports. Further, special methods for modulating either the source frequency or the resonant frequency of the resonator are disclosed which avoids the need to sweep the source frequency through the resonance of the resonator.

Heath's invention uses a half wavelength microstrip resonator which is tightly sandwiched between two sheets of the sample test material. In turn, these sheets of test material are clamped in a special fixture. The microstrip resonator is loosely capacitively coupled to a microstrip line which passes near one end of the resonator normal to the resonator length. The dielectric constant is determined from measurements of the resonant frequency and Q-factor for transmission between the sensor's two input and output ports. Since special cutting and positioning of thin sheets of the sample material in the test fixture is required, Heath's method is not in situ or nondestructive.

Both Flemming and Heath's inventions involve transmission from an input port to an output port, both ports being loosely or weakly coupled to the intervening resonator by capacitive coupling. In comparison, the present invention utilizes the reflected wave from one port only, said single port being much more strongly coupled to the resonator. This coupling is, in fact, near critical such that the source port is reasonably well matched to the resonator at the resonant frequency. Besides being simpler through the elimination of one port, the near critical coupling feature of this present invention permits determining the real ($\epsilon'$) and the imaginary ($\epsilon''$) components of the test material dielectric constant simultaneously and independently. Moreover, near critical coupling permits measurement of the resonant frequency with exceptionally high accuracy and resolution. As a result, the present invention can resolve extremely small changes in $\epsilon'$, even when the Q-factor is low, i.e., when the test material is very lossy. Such measurements for low Q-factors are much more difficult or impossible when using such transmission resonators.

Gerhard's invention is a microstrip one-port reflection resonator sensor intended only for measurement of the real dielectric constant ($\epsilon'$) of thin microwave substrate material samples. The test materials are cut into samples suitable for fitting into a special fluid-(e.g., air) pressurized fixture for forcing the test dielectric against a thin substrate film on which the metal resonator is formed. Thus, Gerhard's invention is not in-situ or nondestructive. Moreover, there are many other distinct differences in the construction, operation, and the single use of Gerhard's invention compared to the broad range of uses of the present invention. In particular, Gerhard does not recognize the significance and importance of sensor losses in order to achieve near-critical coupling between the microwave source and the input to his invention. As noted above, this permits measurement of the dielectric loss factor ($\epsilon''$) and the real dielectric constant ($\epsilon'$) of the thin sheet of the test material with the greatest possible accuracy and resolution.

Besides measurement and monitoring the dielectric properties of materials using previously undiscovered microstrip reflection resonator sensor configurations, the present invention can also be used to measure or monitor the conductance of highly conducting materials. This application of microstrip resonators, operating in either the reflection or transmission modes, has not been previously discovered.

SUMMARY OF THE INVENTION

The invention is method and apparatus for measuring or monitoring the complex dielectric and dissipative properties of materials in situ. A reflection sensor having a highly conducting microstrip resonator formed therein is placed in contact with the material being measured. At the resonant frequency of the resonator, the electromagnetic fields on the face of the sensor become exceptionally large and couple most strongly to the test material. In turn, dielectric and dissipative properties of the test material have a strong effect on the sensor's resonant frequency and its normalized input resistance mismatch or coupling factor at resonance. By measuring the reflected wave at the sensor input as the source frequency is swept, both the resonant frequency ($f_r$) and the input resistance mismatch or coupling factor ($r_o$) are measured to independently determine the real ($\epsilon'$) and imaginary ($\epsilon''$) parts of the complex dielectric constant, or the conductivity ($\sigma$) of highly conducting materials.

An important and unique advantage of using a reflection resonator sensor of the present invention depends on having near-critical (well matched) coupling at the sensor input. Critical coupling refers to having $r_o=1$. When $r_o<1$, the sensor is said to be undercoupled, and it is overcoupled when $r_o>1$. Regardless of the properties of the test material, it will be seen that the sensor can always be designed or adjusted so that $r_o$ is nearly unity. Under this condition, the sensor's input reflection coefficient (or return loss) is nearly zero at the resonant frequency, $f_r$, and nearly unity at frequencies far removed above and below $f_r$. Therefore, as the source frequency is swept, the return loss dips to an extremely sharp minimum at $f_r$, and the sharpness of this dip depends on having $r_o$ close to unity. For example, the return loss dips to $-\infty$ dB at resonance when the sensor is critically coupled ($r_o=1$) to the source. Similarly, when $0.9<r_o<1.1$ at $f_r$, the return loss is smaller than $-25.6$ dB, compared to frequencies far removed from resonance where the return loss is zero dB. In comparative contrast, if the input coupling is weak, e.g., $r_o=0.1$, then the dip in the return loss is only $-1.74$ dB at $f_r$. Unless the resonator Q-factor is exceptionally high, it would be impossible to measure $f_r$ with any degree of accuracy and resolution from an observed spectral sweep on the screen of a network analyzer. It is therefore clear that the dip in return loss at $f_r$ becomes extremely sharp as $r_o$ approaches unity. This permits measurement of $f_r$ and $r_o$ (and hence determination of small variations in $\epsilon'$, $\epsilon''$ or $\sigma$ of the test material) with exceptionally high accuracy and resolution.

When the invention is applied to dissipative (lossy) dielectrics variations in the test material loss factor $\epsilon''$ cause $r_o$ to vary inversely with $\epsilon''$. Conversely, when the invention is applied to highly conducting materials, increasing conductivity $\sigma$ causes $r_o$ to also increase. Consequently, to maintain $r_o$ within a desired range or window which will permit acceptable accuracy and resolution in the measurement of $f_r$ requires proper design of the sensor sensitivity to anticipated variation in $\epsilon''$ or $\sigma$. Thus, the practical implication is that each sensor must be uniquely tailored for the dielectric properties of the particular material to be measured.

OBJECTS AND ADVANTAGES

Accordingly, the following objects and advantages of the invention are claimed:

To provide highly sensitive direct-contact sensors for the purpose of measuring or monitoring the relative complex permittivity components ($\epsilon'$, $\epsilon''$) or conductivity ($\sigma$) of materials in situ and nondestructively at microwave frequencies. When used in conjunction with a suitable low power (a few mW) swept microwave frequency source and microwave detection system, each measurement can be made very quickly (a few milliseconds). Consequently, the sensor is ideally suited to real time control of manufactured products comprised of many forms of dielectric materials such as solids, resins, liquids, powders and gasses, or of conductive materials such as carbon fibers, composites or ceramics containing carbon or metals, metals or superconductors. Being small, rugged and having a smooth face, the sensor can readily be conformably configured into a wall, chute or glide sled to monitor materials passing over or under its surface at a high rate, such as powders, grains, and liquids, or conducting materials such as fibers, wires, etc. It can be conformably mounted in a mold or platen to monitor dynamic changes in the dielectric properties of a material undergoing chemical and physical changes.

As applied to dielectric materials, a major advantage of the invention is its ability to monitor small changes in $\epsilon'$ with exceptionally high resolution. Depending on sensor design, a resolution of one part in 1000 is possible. The invention is therefore particularly well-suited for monitoring the constituent dielectric components in the material. For example, most dielectric materials are comprised of materials having different dielectric constants. Changes (e.g., contamination, decomposition or change in volume fraction) in one of the constituent materials causes a change in the total bulk dielectric constant of the whole material. Such changes can be detected by the sensor, signaling the change in one or more of the constituents. For example, the invention has been used to quantify the amount of unburned carbon in flyash. As a further example, the sensor is particularly sensitive to the presence of extremely small quantities of free or bound moisture in a material. This is because moisture is a polar substance having an unusually large real dielectric constant. For free water, $\epsilon'$ ranges from 55 to 78 depending on the microwave frequency, whereas most other dielectric substances have dielectric constants ranging from 1 to 6. Consequently, the presence of only a few parts/million of moisture in a dielectric material can be detected. For example, this invention is being used to detect less than 50 parts/million of homogenized moisture in synthetic petroleum products (hydraulic fluids). In other applications, the invention is being used to measure wet and dry densities, and hence the moisture content, of such agricultural products as food grains, chopped onions and garlic, and forages, and of such wood products as solid wood, manufactured composite boards (particleboard, flakeboard, fiberboard, etc.), and wood particles, pellets, flakes and chips. Being small, rugged and having a smooth face, the sensor can be rapidly scanned over the surface of a solid dielectric media such as plastic, composite or ceramic objects. Being highly sensitive, the sensor is able to detect local changes in the bulk dielectric properties which are indicative of physical properties such as the presence of moisture, porosity, voids, cracks, seams and other anomalies. Because of the penetrating nature of the electromagnetic fields around the microstrip resonator which is a part of the sensor, the sensor is able to detect these anomalous features to depths of the order of $L/2$, where L is the physical length of the resonator. For the fundamental or lowest order resonance, $L=\lambda/2$ where $\lambda$ is the wavelength in the effective dielectric surrounding the resonator.

By shaping the resonator as a dipole, the electromagnetic fields near to the sensor face can be made to be highly polarized. This property can be used to good advantage to detect the dielectric or conductive anisotropy of a material. For example, it can be used to measure the grain direction of solid wood or the fiber direction in fiber (conductive or nonconductive) reinforced advanced composites, or the direction of microscropic cracks in conductive materials.

Another example of successful application of this invention is to monitoring the dynamic curing process of thermoset and thermoplastic resins. During the cure of such polymer materials, both $\epsilon'$ and $\epsilon''$ change over wide ranges. When monitored by the sensor which is part of a conformal mold, the state of material cure can easily be tracked versus time and temperature. Being configured of materials which are able to sustain high temperatures, the sensor can be used in a high temperature mold or autoclave. The physical parameters which can be tracked are the viscosity of the resin and the rate of cure. Further, data obtained from this sensor can be used to predict the degree of final cure long before it occurs. This is very useful information because it signals control changes that can be made in the cure process in order to achieve a desired degree of cure. These examples are but a few which demonstrate the versatility of the invention.

Further objects and advantages of this invention will become apparent from a consideration of the drawings and ensuing description of it.

LIST OF REFERENCE NUMERALS

2: source of microwave energy for which the frequency can be swept

4: high-directivity directional coupler or reflectometer bridge

6: A or R; microwave envelope detectors

7: coaxial feed cable for feeding short slot 13

8: ratio meter or scalar network analyzer

9: test material for which ($\epsilon'$, $\epsilon''$) or ($\sigma$) is to be measured or monitored 10: basic reflection resonator sensor 11: a, b, c highly conducting microstrip dipole resonators 12: dielectric substrate of thickness $t_1$ having dielectric constant $\epsilon'_{sub}$ 13: electrically short feed slot in ground plane 14

14: ground plane (e.g., copper, aluminum, etc.)

15: resonant slot in ground plane 14

16: microstrip feed line for feeding short slot 13

17: incident wave

18: reflected wave

19: dielectric substrate of microstrip feed line 16

20: basic microstrip reflection sensor with dipole resonator

21: center conductor of semi-rigid coaxial cable 7

22: solder or weld connection of center conductor 21 to ground plane 14

23: solder or weld support connection of coaxial cable 7 to ground plane 14

24: sealed conducting enclosure

25: highly conducting microstrip loop resonator

26: dielectric superstrate of thickness $t_2$ having dielectric constant $\epsilon'_{super}$ 30: basic microstrip reflection sensor with loop resonator 40: basic microstrip sensor with dielectric superstrate 25 added 50: basic microstrip sensor with multiple microstrip dipole resonators 11a, b, c 60: basic resonant slot sensor.

DESCRIPTION OF INVENTION

Operation Of Display Instrumentation

Figure 1:
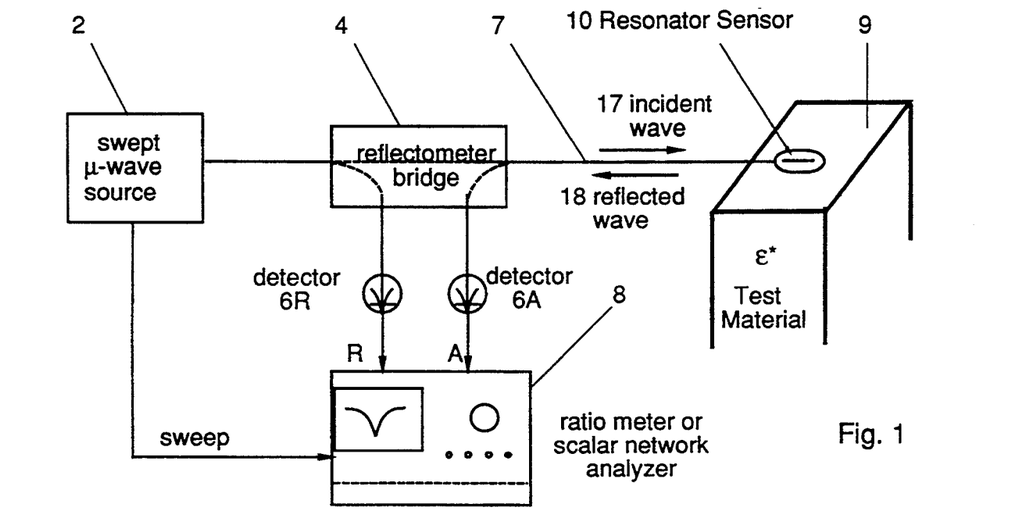
FIG. 1 is a block diagram of a typical microwave reflection resonator sensor measurement system.

FIG. 1 is a block diagram of typical instrumentation used to display and measure the response of a typical microwave reflection resonator sensor 10. The output of the swept frequency source 2 of microwave power (a few mW) is fed to the sensor 10 through a high-directivity bridge or directional coupler 4 via feed cable 7. The bridge or coupler 4 forms a reflectometer for measuring the wave 18 reflected from the sensor 10, relative to the wave 17 incident on the sensor. Typically, the bridge or coupler has a directivity greater than 30 dB and a coupling factor of $-10$ to $-12$ dB. The forward coupled power, which is proportional to the incident wave 17, is envelope detected by detector 6R, the output of which is fed to the reference (R) channel of the ratio meter or scalar network analyzer 8. The reflected wave 18 is coupled to detector 6A and serves as the input to channel A of the ratio meter or analyzer 8. In operation the amplitude of channel A relative to the reference channel R, i.e., the ration A/R, is displayed versus the swept frequency, f, of the microwave source 2. This ratio A/R = $|\Gamma|$ is the magnitude of the complex reflection coefficient $\Gamma$ at the input of sensor 10. $|\Gamma|$ is also commonly referred to as the "magnitude of the $S_{11}$ scattering coefficient" or as the "return loss". $|\Gamma|$ always lies within the range $0 < |\Gamma| < 1$. The lower value corresponds to when the sensor impedance is perfectly matched to the source such that there is no reflected wave 18, i.e., when sensor 10 is critically coupled to source cable 7 at the resonant frequency, $f_r$, of sensor 10. The upper value corresponds to when the frequency f of source 2 is far removed from $f_r$.

In use, sensor 10 is brought in physical contact with test material 9 for which the real and imaginary components of the complex dielectric constant $\epsilon^*$ ($=\epsilon' - j\epsilon''$) or the conductivity $\sigma$ are to be measured or monitored. As the frequency of source 2 is swept, the measured ratio $|\Gamma| = $ A/R dips to a sharp minimum at $f_r$, as observed on the display screen of the ratio meter or scalar network analyzer 8. $|\Gamma|$ is mathematically related to the input impedance Z of sensor 10 according to $$|\Gamma| = \left| \frac{z-1}{z+1} \right| \tag{1}$$

where $z = Z/R_c$ is the input impedance Z normalized by the characteristic resistance $R_c$ of source cable 7. Further, $|\Gamma|$ is usually expressed in decibels (dB) according to $$|\Gamma| \text{ in dB} = 20 \text{ Log } |\Gamma| = 20 \text{ Log } \left| \frac{z-1}{z+1} \right| \tag{2}$$

When the frequency, f, of source 2 is equal to the resonant frequency, $f_r$, of sensor 10, $z = r_o$ is real and equal to the sensor's input mismatch or coupling factor. If the sensor 10 is nearly critically coupled ($r_o = 1$), then $|\Gamma| = -\infty$ dB according to Eq. (2). Also, at frequencies far removed from resonance, z ($=jx$) is purely reactive so $|\Gamma| = 1$, or zero dB. Thus, $0 < |\Gamma| < 1$ maps into $-\infty < |\Gamma|$ (in dB) $< 0$ according to Eq. (2). Note that if $r_o$ for the sensor 10 is designed for near-critical coupling, a sharp, well-defined dip at $f_r$ is observed on the logarithmic (dB) display of the ratio meter or scalar network analyzer 8, even though the Q-factor of sensor 10 may not be large. Of course, having a large Q-factor also contributes to the sharpness of the displayed dip at frequencies near to $f_r$.

For a single resonant mode (e.g., fundamental, 2nd, 3rd, etc.), sensor 10 can be regarded as a parallel $R_oLC$ network which is coupled to source cable 7 by a perfect n:1 transformer. The resonant frequency $f_r$ is given as $$f_r = \frac{1}{2\pi\sqrt{LC}} \qquad (3)$$

where L and C are the effective inductance and capacitance of the resonator mounted within sensor 10.

The electromagnetic fringing fields on the sensor face can be made to couple with the test material 9 in two ways:

A. Capacitive Coupling wherein the real dielectric constant ($\epsilon'$) of material 9 primarily affect the capacitance C in Eq. (3). Compared to when sensor 10 is situated in air, positioning of a nonmagnetic dielectric test material 9 against the sensor 10 causes C to increase, yielding a corresponding decrease in $f_r$ according to Eq. 3. For this method of coupling sensor 10 is designed such that the fringing electric field of the sensor is the dominant coupling field to test material 9.

B. Inductive Coupling is useful for measuring the conductive properties ($\sigma$) of highly conductive test materials. For this application, the fringing magnetic field of sensor 10 induces eddy currents in the conductive material 9. By Lenz's law, the mutual inductive coupling between the resonator in sensor 10 and the conductive material 9 causes a decrease in the effective inductance L of the resonator. As seen from Eq. (3), this causes the resonant frequency, $f_r$, to increase with the conductance of test material 9. In such applications, sensor 10 is normally designed to minimize the capacitive coupling (A above) while maximizing the mutual inductive coupling.

Inductive coupling to a magnetic test material causes L to increase in a manner dual to capacitive coupling to a dielectric material as discussed in A above.

The following focuses first on capacitive coupling (A) where the electromagnetic fringing fields on the face of sensor 10 are coupled into a dielectric test material 9. To a first order, the effective capacitance C is given by $$C = C_o K(\epsilon' - 1) \qquad (4)$$

where K is a fringing field constant and $C_o$ is the effective capacitance when the sensor is in air ($\epsilon' = 1$). Assuming that test material 9 is nonmagnetic, the inductance L is constant. Then, using Eq. (4) in Eq. (3), it is seen that $f_r$ decreases with $\epsilon'$ of the test material 9 with slope $$\frac{\partial f_r}{\partial \epsilon'} = \frac{-K}{2C_o} f_r \qquad (5)$$

Although not necessary, sensor 10 is usually designed so that $K/C_o \ll 1$. In this case, $f_r$ decreases linearly with increasing $\epsilon'$ of dielectric test material 9.

The secondary resistance $R_o$ of the equivalent parallel $R_oLC$ network representing sensor 10 includes the effects of all losses. Since the test material 9 is in close physical contact with the face of sensor 10, the dissipative losses of test material 9 are dominant over the radiation and dissipative losses of sensor 10. Assuming this to be the case, analysis shows that $$R_o = \frac{N\sqrt{C}}{\epsilon''} \qquad (6)$$

where N is a constant and $\epsilon''$ is the loss factor of test material 9. Since $C_o/K$ is small, C has a weak dependence on $\epsilon'$ of test material 9. Thus, $R_o$ is essentially inversely determined by $\epsilon''$.

At resonance, $R_o$ is transformed through the transformer as $n^2 R_o$ at the input to sensor 10 where n:1 is the effective turns ratio. When this transformed resistance is normalized by the characteristic resistance $R_c$ of the source cable 7, the previously mentioned coupling or input mismatch factor $$r_o = n^2 R_o / R_c = \frac{n^2 N \sqrt{C}}{\epsilon''} \qquad (7)$$

is defined in terms of $\epsilon''$ of dielectric test material 9. From the reflection coefficient $|\Gamma|$ as measured at $f_r$ using ratio meter or scalar network analyzer 8, Eq. (2) can be inverted to find $r_o$, $$r_o \text{ or } r_o^{-1} = \frac{1 - 10^{|\Gamma|/20}}{1 + 10^{|\Gamma|/20}} \qquad (8)$$

where $|\Gamma|$ is measured in negative dB. However, note that Eq. (2) is double-valued, i.e., both $r_o$ and $r_o^{-1}$ give the same value of $|\Gamma|$, depending on whether sensor 10 is overcoupled ($r_o > 1$) or undercoupled ($r_o < 1$). Consequently, the choice of $r_o$ or $r_o^{-1}$ in Eq. (8) is made based on knowledge of whether sensor 10 is over- or undercoupled. This determination can be made in several ways, the simplest by lifting the sensor 10 slightly from the surface of test material 9. Doing so causes the effective $\epsilon''$ to decrease and $r_o$ increases in Eq. (7). If the corresponding displayed $|\Gamma|$ decreases (moves in the negative direction) sensor 10 is undercoupled ($r_o < 1$); conversely, if the displayed $|\Gamma|$ increases, then sensor 10 is overcoupled ($r_o > 1$). Once over- or undercoupling is established, it is not difficult to track $r_o$ as $\epsilon''$ of dielectric test material 9 changes.

In order to measure $f_r$ with high resolution, the reflection coefficient magnitude $|\Gamma|$ at $f_r$ must be sufficiently small so as to display a sharply defined resonance. Typically, we require that $|\Gamma| < -10$ dB, which dictates that $r_o$ lie in the 4:1 window, $0.5 < r_o < 2.0$ according to Eq. (2). This translates into a corresponding dynamic range over which $\epsilon''$ can be accurately measured according to Eq. (7). In practice, the equivalent turns ratio n in Eq. (7) can be adjusted in the design of sensor 10 so as to achieve the desired $r_o$ for a given $\epsilon''$ of test material 9. How this can be done is discussed in the Operation of Invention.

Calibration of sensor 10 is simply accomplished using air and one "standard" test material having known $\epsilon_s'$ and $\epsilon_s''$. Let $f_a$ and $f_s$ be the resonant frequencies when sensor 10 is located in air and when placed against the calibration "standard," respectively. Then, using Eq. (3) and (4), the ratio $C_o/K$ is found, $$C_o/K = \frac{\epsilon_s' - 1}{(f_a/f_s)^2 - 1} \quad (9)$$

Having found $C_o/K$, the unknown real dielectric constant for test material 9 is determined as $$\epsilon' = 1 + \frac{C_o}{K}\{(f_a/f_r)^2 - 1\} \quad (10)$$

where $f_r$ is the resonant frequency when sensor 10 is positioned against dielectric test material 9. In certain instances, the resonant frequency when sensor 10 is located in air cannot be measured because the corresponding $r_o$ is too large. In this event, it is possible to use a second "standard" dielectric having an $\epsilon_s''$ which gives an acceptable $r_o$, e.g., one for which $0.5 < r_o < 2.0$. Eq. (9) and Eq. (10) can then be accordingly modified for this case to find $C_o/K$ for that second standard, and to determine $\epsilon'$ of dielectric test material 9.

To determine $\epsilon''$ of dielectric test material 9, take the product $f_r r_o$ using Eq. (3) and Eq. (7), $$\epsilon'' = N'/f_r r_o \quad (11)$$

where $N'$ ($=n^2N/2\pi L^{\frac{1}{2}}$) is a constant which can be found by positioning sensor 10 against the "standard" calibration material having known $\epsilon_s''$, resonant frequency $f_s$ and coupling factor, $r_{os}$, $$N' = \epsilon_s'' f_s r_{os} \quad (12).$$

In some applications it is not necessary to find the absolute value of $\epsilon''$ of dielectric test material 9. Such a case arises, for example, when measuring the moisture content and the dry density of test material 9. In such cases, it is sufficient to know $\epsilon''/N'$, i.e., to know how $\epsilon''$ varies (within constant $N'$) as a function of the moisture content and dry density.

From the preceding discussion note that $\epsilon''$ (or $\epsilon''/N'$) for a reflection resonator of this invention can be found without need for measurement of the sensor unloaded $Q_o$-factor. Measurement of $Q_o$ for reflection resonators is somewhat complicated, (see Ginzton, R. L., *Microwave Measurements*, McGraw Hill, 1957, pp. 407-415) and not readily automated. It first involves measurement of $f_r$ and $r_o$, performing some calculations to determine the half-power reflection coefficients, then measuring the bandwidth ($\Delta f$) between these coefficients and finally calculating $Q_o = f_r/\Delta f$. However, it turns out that if $r_o$ is measured there is no need to measure $Q_o$. Conventional measurements using two-port transmission resonators require the unloaded $Q_o$-factor in order to determine $\epsilon''$. Here, "unloaded" refers to the Q-factor with the loading effects of the input and output ports removed; hence, the need for weakly coupled input and output ports previously mentioned.

For the present invention, it is easily shown that $r_o$ provides the same information about $\epsilon''$ as does the unloaded $Q_o$-factor, without the requirement of weak coupling. The "unloaded" $Q_o$-factor of a one- or two-port resonator is $Q_o = 2\pi f_r R_o C$. Using Eq. (3) and Eq. (6)

$$Q_o = \frac{NC}{L^{\frac{1}{2}}\epsilon''} = \frac{PC}{\epsilon''} \quad (13)$$

where P is a constant. Comparing Eq. (7) and Eq. (13), it is noted that $r_o$ and $Q_o$ have the same inverse relation to $\epsilon''$. In fact, since $C_o/K$ in Eq. 4 is normally large compared to unity, the capacitance C in Eq. (7) and Eq. (13) is essentially constant, so functionally $Q_o$ and $r_o$ behave in a nearly identical manner irrespective of $\epsilon'$ of test material 9.

In applications of the invention to the measurement or monitoring of highly conducting test materials 9, sensor 10 is normally designed to minimize capacitive coupling (A above) while maximizing mutual inductive coupling (B above) between sensor 10 and conducting test material 9. In this case, the magnetic field around the resonator within sensor 10 induces large eddy currents in the conductive test material 9 at resonance. By Lenz's law, these currents produce a magnetic field of their own which opposes the inducing magnetic field. The result is a net reduction in the resonator inductance L in Eq. (3). Increasing the conductance of test material 9 allows increased induced eddy currents, and a further reduction in L. Thus, the resonant frequency $f_r$ increases with increasing conductance or conductivity $\sigma$ of test material 9.

Mathematical analysis of this type of coupling is by no means straightforward because it strongly depends on many interactive factors including the size, shape and conductive properties of test material 9. It is sufficient to remark that $f_r$ and $r_o$ increase nonlinearly with conductivity $\sigma$, everything else being constant. It is always possible to design and adjust reflection resonator sensor 10 for near-critical coupling. Calibration is achieved using materials of known conductivity $\sigma$.

Sensor Configurations

Figure 2:
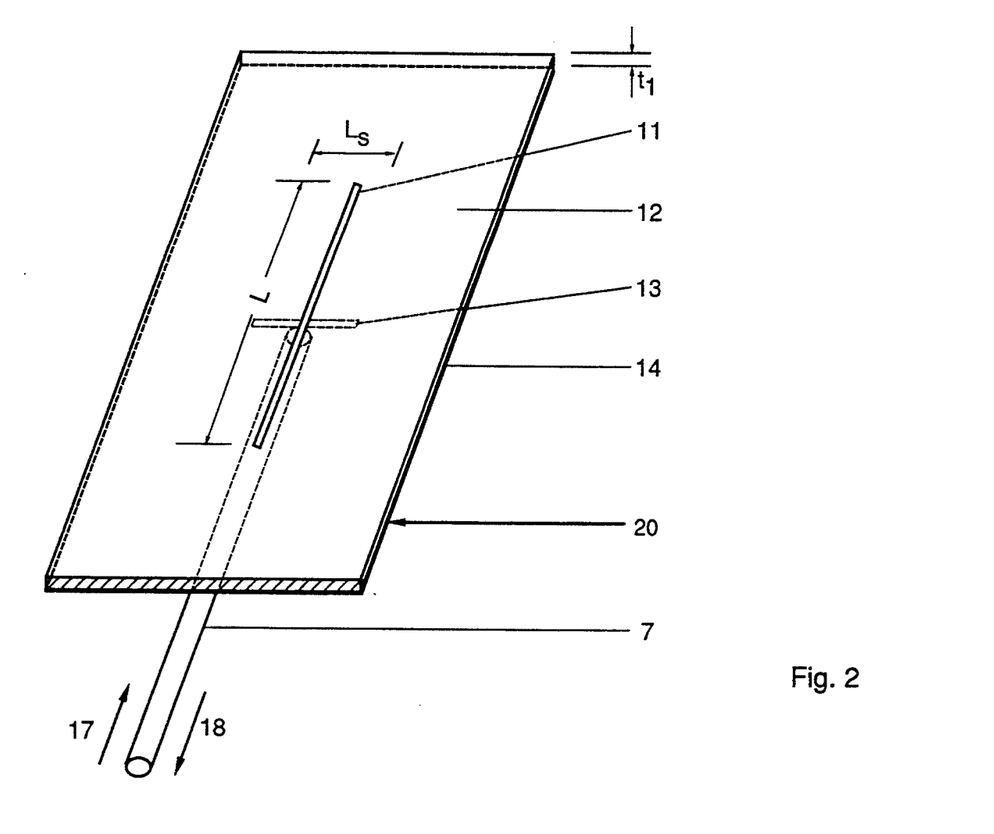
FIG. 2 shows a basic microwave reflection dipole resonator sensor.

The basic preferred embodiment of the invention, shown in FIG. 2, is relatively simple. The parts comprising the basic sensor 20 consist of a highly conducting (e.g. metal) microwave resonator 11 of length L which is etched or otherwise fastened to the surface of a dielectric substrate 12 of thickness $t_1$ and dielectric constant $\epsilon'_{sub}$. In turn, the dielectric substrate 12 is bonded (on the surface opposite to resonator 11) to a metal ground plane 14. The resonator 11 is electromagnetically coupled by means of mutual inductive coupling to an electrically short feed slot 13 of length $L_s$ in the ground plane 14. $L_s$ is substantially shorter than L which is one half wavelength long at the fundamental or first resonance mode. Feed slot 13 is centered and oriented substantially perpendicular to resonator 11. Further, the short feed slot 13 is electrically coupled to a feed line 7, e.g., a miniature semi-rigid coaxial cable which extends from the directional coupler or reflectometer bridge 4 in FIG. 1.

In all of the figures pertaining to this invention, the wave incident on the feed line 7 is denoted as 17, while the wave reflected from the feed line is denoted as 18. In application of the sensor, it will be seen that the features of the reflected wave 18 as the frequency of the source 2 in FIG. 1 is swept are used to determine the resonant frequency, $f_r$, and the coupling factor, $r_o$, at the sensor input. As previously shown, $f_r$ and $r_o$ are related to the dielectric or the conductive properties of the test material 9.

Figure 3A:
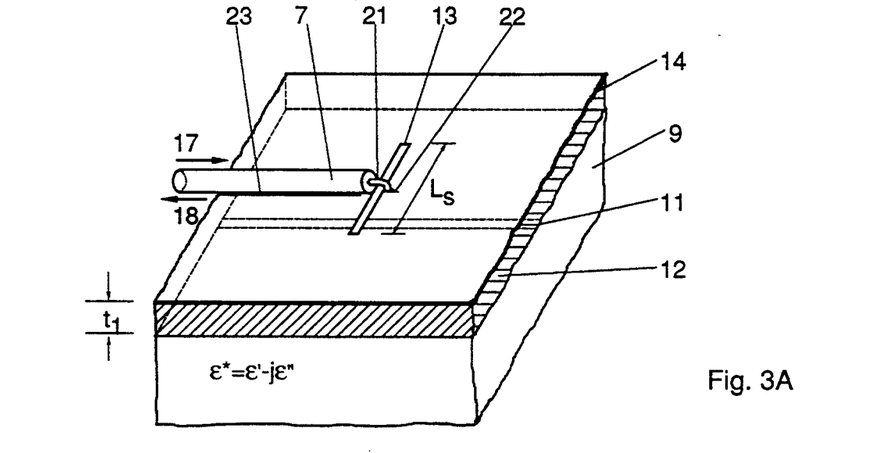
FIGS. 3A–C illustrate a microwave reflection resonator sensor in contact with a test material, with three alternative methods for coupling the feed line to the sensor feed slot.
Figure 3B:
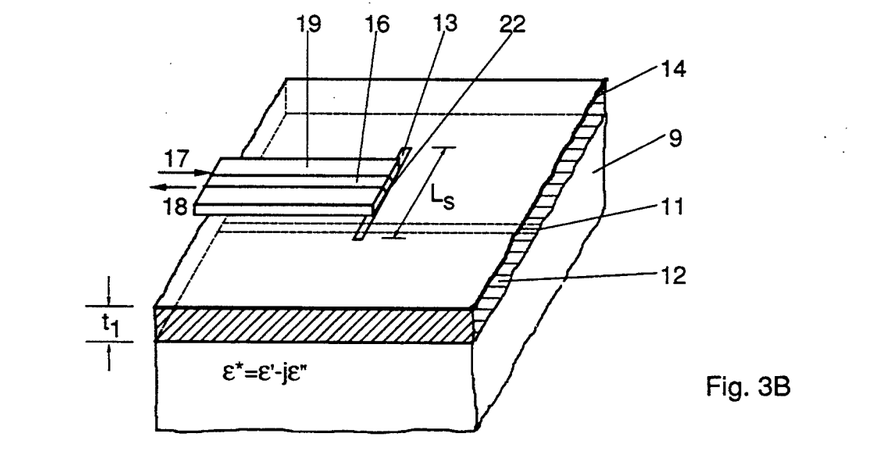
Figure 3C:
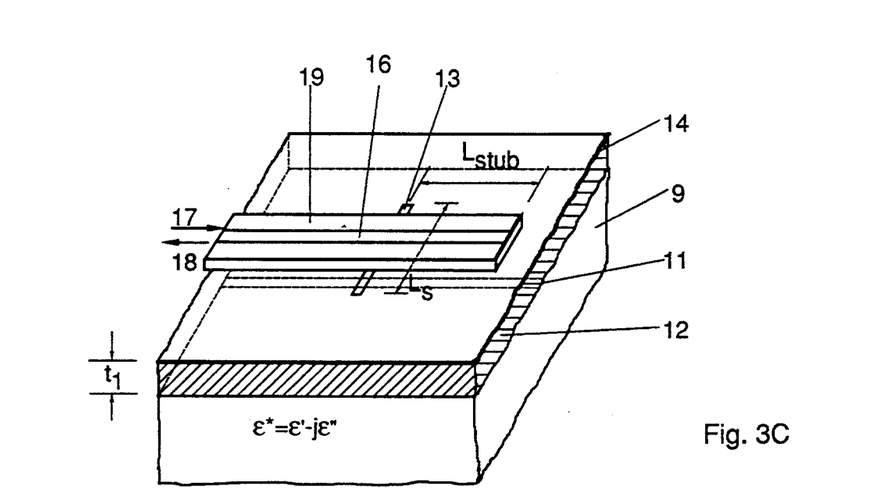

FIG. 3A depicts the microstrip sensor making physical contact along its front face (with resonator 11) with the test material 9 having complex dielectric constant $\epsilon^*$ ($=\epsilon' - j\epsilon''$). This is the normal configuration for operation of the invention when being used to measure dielectric properties. Three of many alternative methods for feeding short slot 13 are shown in FIGS. 3A,B,C.

When using a coaxial cable 7 as in FIG. 2, coupling to the short slot 13 is accomplished by simply extending the cable center conductor 21 across the slot 13 by means of a solder connection 22, as detailed in FIG. 3A. The shield of the semi-rigid coaxial cable 7 is electrically connected to the ground plane 14 by soldering or welding at points 23 along its length. Similarly, FIG. 3B shows the short slot 13 being fed by a section of microstrip line 16 which is etched on dielectric substrate 19. The end of microstrip line 16 is extended across slot 13 and connected to ground plane 14 where it is electrically connected by soldering or welding at point 22. In FIG. 3C, a microstrip line 16 on substrate 19 is extended across and beyond short slot 13 to form an open-ended stub of length $L_{stub}$. In FIGS. 3A,B,C, coaxial feed cable 7 or microstrip line 16 on substrate 19 extend to a suitable connector (not shown) which connects to the reflectometer bridge or directional coupler 4 in FIG. 1.

Figure 4:
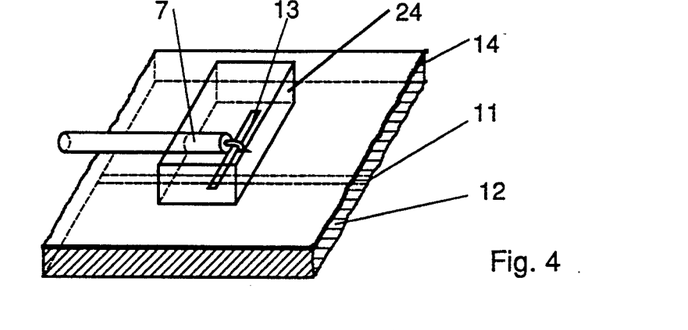
FIG. 4 shows a sensor feed slot enclosed in a shielding cavity.

To minimize electromagnetic radiation from the short feed slot 13 on the back side (ground plane 14) of the sensor 10, the short feed slot may be enclosed in a shielding cavity 24 as shown in FIG. 4. The perimeter of shielding cavity 24 is electrically connected to ground plane 14.

Figure 5:
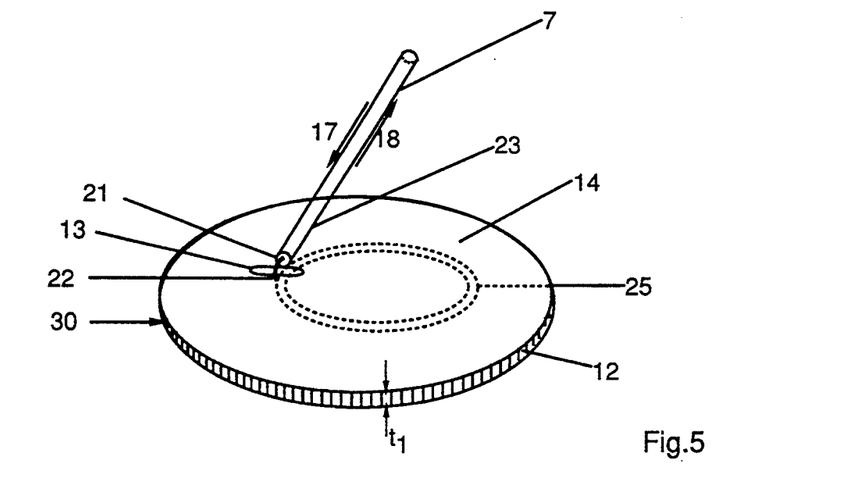
FIG. 5 shows a basic microwave reflection loop resonator sensor.

The highly conducting microstrip resonator can have a variety of shapes. Commonly used shapes are the dipole 11 in FIGS. 2, 3 and 4, the loop 25 in FIG. 5, or a rectangle, a disc, a bow-tie, etc. (not shown). The resonator shape is chosen according to the desired polarization and pattern of the fringing field at one of the resonant modes. For example, the dipole 11 shape is particularly useful for measuring the directional dielectric properties of an anisotropic test material 9 because the fringing electric field is highly polarized parallel to dipole 11. The dipole shape is also highly sensitive to surface cracks in test material 9. In contrast, the loop resonator 25 in FIG. 5 tends to average the local dielectric anisotropy of test material 9 because the fringing electric field pattern is circular.

Figure 6:
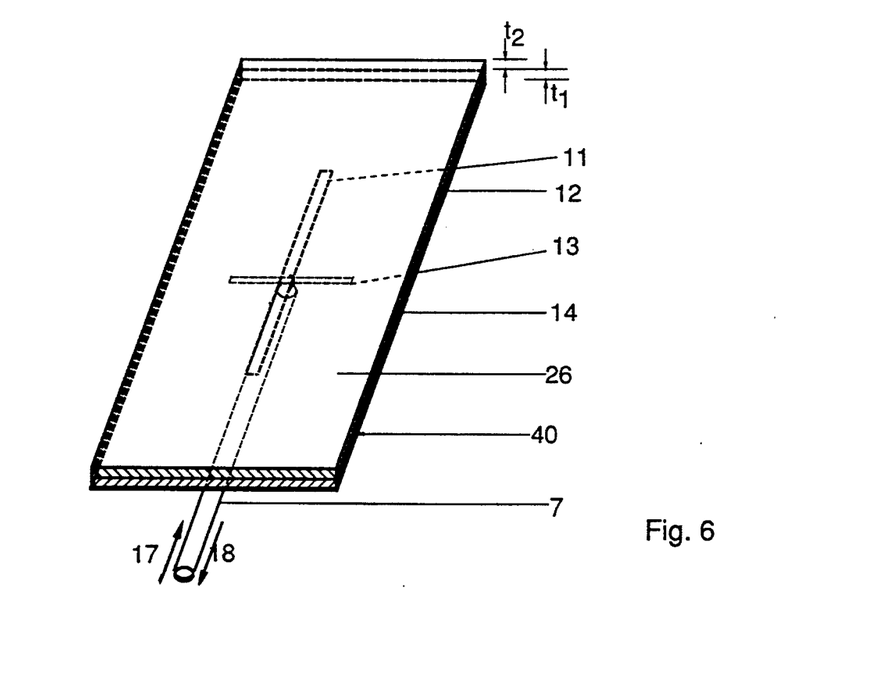
FIG. 6 illustrates a sensor having a thin dielectric superstrate over the resonator.

FIG. 6 shows the same embodiment as FIG. 2 except that a thin dielectric superstrate 26 of thickness $t_2$ and dielectric constant $\epsilon_{super}$ has been added to the face of sensor 40, thereby sandwiching resonator 11 between substrate 12 and superstrate 26. The purpose of superstrate 26 is to diminish the capacitive coupling of resonator 11 to test medium 9, and to protect resonator 11 from wear and damage. Superstrate 26 can be used for any of the other resonator shapes, e.g., to sandwich the loop 25 in FIG. 5 between substrate 12 and superstrate 26.

Figure 7:
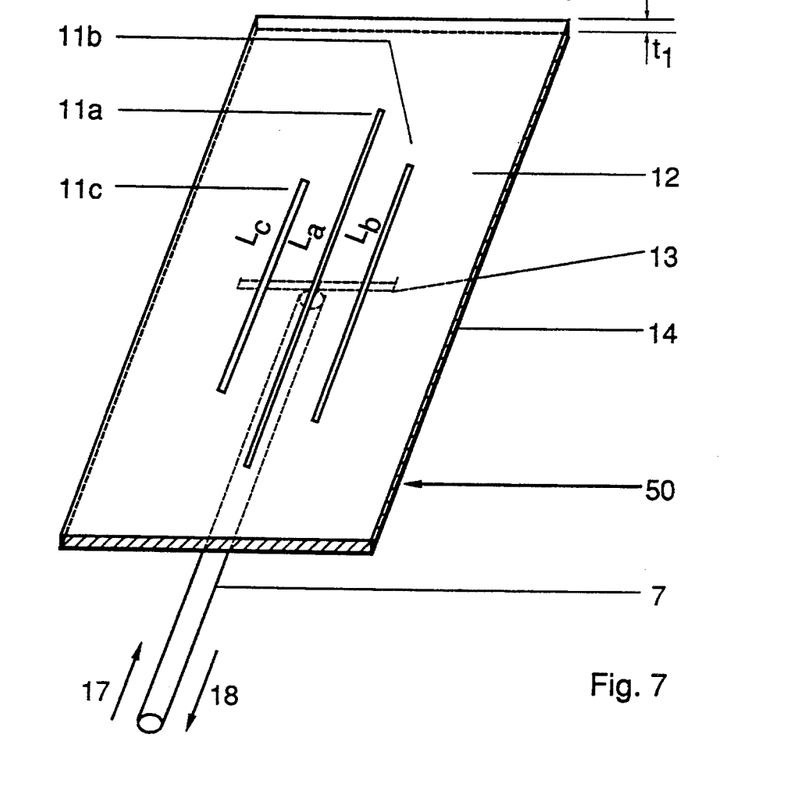
FIG. 7 shows a sensor with multiple dipole resonators of different lengths driven from a single feed slot.

FIG. 7 shows an embodiment of the invention (sensor 50) in which multiple microstrip resonators 11a, 11b and 11c are added, each having different corresponding lengths $L_a$, $L_b$, and $L_c$ so as to resonate at different frequencies. All of the resonators are driven from a single common electrically short slot 13.

Figure 8:
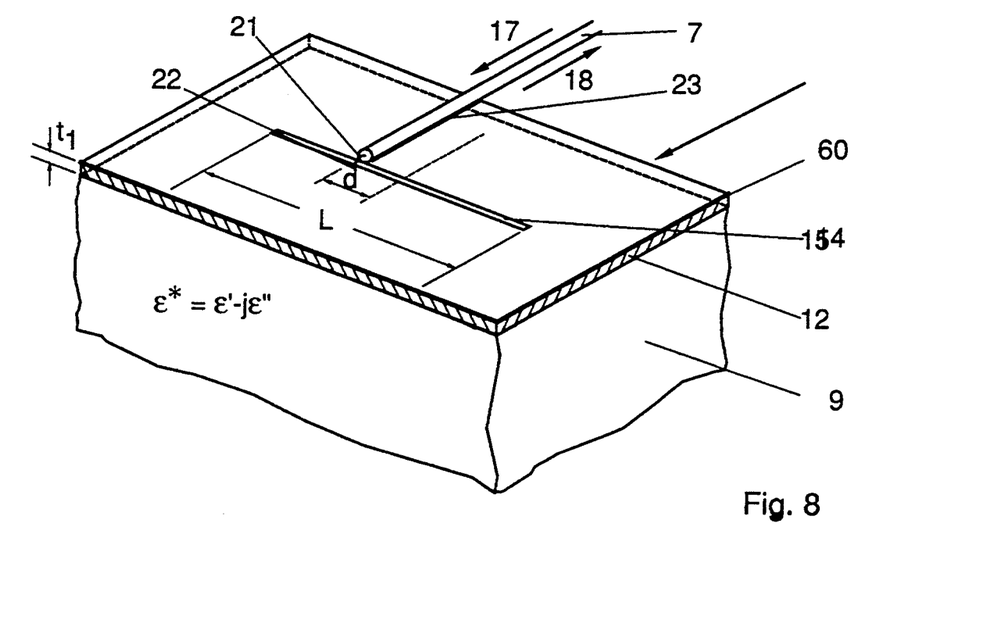
FIG. 8 illustrates a sensor in which the resonator is a slot in the ground plane.

FIG. 8 shows the sensor 60 in which slot 15 of length L in the ground plane 14 becomes the resonator itself, without the need for a highly conductive resonator. Here, the slot length L is much longer than $L_s$ for the embodiments shown in FIGS. 2-7 where short slot 13 inductively couples to the conducting resonator. In the embodiment 60 in FIG. 8 the dielectric substrate 12 plays the same role as the dielectric superstrate 26 in FIG. 6, i.e., it reduces the capacitive coupling between the resonant slot 15 and test material 9.

Operation of Invention

In operation, a microwave source 2 capable of producing a few milliwatts of microwave power is connected to any of the sensors via directional coupler or reflectometer bridge 4 of FIG. 1 and the coaxial cable feed line 7 in FIGS. 2, 3A, 4-8 or microstrip line 16 in FIGS. 3B and C. In FIGS. 2, 3A, 4-7, the incident wave 17 electromagnetically excites the short feed slot 13 by means of the coaxial cable center conductor 21 or in FIG. 3B by the microstrip line 16. In FIG. 3C, the standing wave on the microstrip line 16 couples to the short slot 13. Here, the end of microstrip line 16 may be open or short circuited with a corresponding adjustment of $L_{stub}$. The resulting electromagnetic fields in the immediate neighborhood of the electrically short slot 13 inductively couples to the highly conductive (e.g., metal) microstrip dipole resonator 11 in FIGS. 2-4 and 6, or loop 25 in FIG. 5. The dipole 11 or loop 25 is etched on the surface of the dielectric substrate 12 having thickness $t_1$ and real dielectric constant, $\epsilon'_{Sub}$. When the frequency of the microwave source is swept, the dipole 11 or loop 25 resonates at a frequency which strongly depends on the construction of the sensor 20 in FIG. 2, 30 in FIG. 5, 40 in FIG. 6, or 50 in FIG. 7. In FIG. 8 where the incident wave 17 directly excites slot (resonator) 15, it is noted that slot 15 is the equivalent of a resonant magnetic dipole, the dual of an electric dipole. The magnetic filed is, therefore, parallel to the magnetic dipole (slot 15). Consequently, the configuration in FIG. 8 is well suited to measuring magnetic test materials and their anisotropic properties.

In practical use for the purpose of measuring or monitoring the dielectric properties of various test dielectric materials 9, the sensors are caused to make close physical contact with the test material, as depicted in FIGS. 1, 3, and 8. In the case of a solid material, the sensor is pressed firmly against a smooth surface. For liquids, gasses or other flowing materials such as powders, the sensor is immersed in the material, or the material is made to flow over the sensor face.

When coaxial feed cable 7 in FIGS. 2, 3A, 4-7 or microstrip feed line 16 in FIGS. 3B or 3C are nearly critically coupled to short feed slot 13, the amplitude of wave 18 reflected from the slot 13 dips to a sharp minimum at $f_r$ as the frequency of the source is swept. With proper adjustment of the length $L_s$ of the short feed slot 13, or of the position of the dipole 11 or loop 25 relative to that of slot 13 in FIGS. 2-7, the resistance presented to the coaxial feed line 7 or microstrip feed line 16 can be made to be nearly equal to the characteristic impedance of the feed line (e.g., 50 ohms) at $f_r$. Similarly, in FIG. 8 the resistance that resonant slot 15 presents to the coaxial feed line 7 is adjusted for a good impedance match at $f_r$ by positioning the feed connection 22 at distance d along the axial centerline of the slot. These adjustments result in a very sharp minimum of the reflected wave 18 at resonance. When observed by means of a reflectometer arrangement as depicted in FIG. 1, $f_r$ can be measured with great precision, typically to a resolution of at least 1 part in $10^6$.

This good impedance match at $f_r$ is referred to as "near-critical coupling" as discussed in detail in the section Operation of Display Instrumentation. This condition is crucial to the operation of the invention since it determines the accuracy and resolution with which the dielectric or conductive properties of test material 9 can be measured.

The effective depth to which the reactive electromagnetic fields around the resonator 11 penetrate into a test medium 9 having low ($\epsilon'$, $\epsilon''$) is about half the resonator length, i.e., L/2.

The preceding discussion has been chiefly concerned with the measurement or monitoring of effects due to variations in the real part $\epsilon'$ of the complex dielectric constant, $\epsilon^*(=\epsilon'-j\epsilon'')$. It has been shown that the resonant frequency $f_r$ is inversely related to $\epsilon'$ according to Eqs. (3) and (4). It has also been noted that $f_r$ and small changes in $f_r$ can be measured with great precision, provided the sensor input is nearly critically coupled to feed lines 7 or 16. Eq. (7) shows that $r_o$ is chiefly determined by the losses in test material 9 and the effective turns ratio n of the feed network which inductively couples to the highly conducting resonator. Therefore two types of coupling are involved in determining $r_o$. While these are not totally independent, they are sufficiently independent for understanding of the principles for design and making effective use of the invention.

The first type of coupling pertains to capacitive (A) and/or inductive (B) coupling between the highly conducting microstrip resonator 11 and the test material 9 as discussed below Eq. (3). Recall that capacitive coupling is useful for measuring or monitoring ($\epsilon'$, $\epsilon''$) of a dielectric test material 9, while inductive coupling is useful for measuring or monitoring ($\sigma$) of a highly conductive test material 9.

In either case, these couplings determine the sensitivities of $f_r$ and $r_o$ to ($\epsilon'$, $\epsilon''$) or ($\sigma$), e.g., the rates of change $\partial f_r/\partial \epsilon'$, $\partial f_r/\partial \sigma$, $\partial r_o/\partial \epsilon''$ or $\partial r_o/\partial \sigma$. These sensitivities are established by the thickness ($t_1$) and dielectric constant ($\epsilon'_{sub}$) of substrate 12 in FIGS. 2-8, by the thickness ($t_2$) and dielectric constant ($\epsilon'_{super}$) of superstrate 26 in FIG. 6, and by the size and shape of the microstrip resonator. For example, for capacitive coupling (A), the capacitance $C_o$ in Eq. (4) is chiefly determined by $t_1$ and $\epsilon'_{sub}$ of substrate 12 in FIGS. 2-7, as well as the width of the dipole resonator 11 or loop resonator 25, while the constant K in Eq. (4) is chiefly determined by $t_2$ and $\epsilon'_{super}$ of superstrate 26 in FIG. 6. As Eq. (5) shows, the sensitivity $\partial f_r/\partial \epsilon'$ is proportional to the ratio $K/C_o$. Thus, with proper choice of the parameters of substrate 12, superstrate 26 or the shape and dimensions of the microstrip resonator, a desired $K/C_o$ ratio can be achieved.

As another example, in the design of a sensor 40 in FIG. 6 for use in measuring or monitoring highly conductive test material 9, it is desired to minimize capacitive coupling (A) by making superstrate 26 relatively thick and having a small dielectric constant $\epsilon'_{super}$. This makes K small so that inductive coupling (B) to test material 9 is dominant.

The second type of coupling pertains to the degree to which the feed source (e.g., coaxial cable 7 or microstrip line 16) is inductively coupled to the microstrip resonator in FIGS. 2-7 or to the resonant slot 15 in FIG. 8. This coupling is quantified by the input coupling or impedance mismatch factor $r_o$. As previously noted, if $r_o=1$ there is no reflected wave 18 from the sensor input and the sensor is said to be critically coupled. It is said to be overcoupled when $r_o>1$ and undercoupled when $r_o<1$. As also previously noted, the operation and use of the invention depends on having near-critical coupling such that $r_o$ always lies within some window which will permit the desired accuracy and resolution for measuring $f_r$. For example, a suitable window might be $0.5<r_o<2.0$. Then, as Eq. (2) shows, the minimum dip in the reflection coefficient $|\Gamma|$ will be lower than $-10$ dB. If greater accuracy and resolution is desired, the width of this window must be reduced.

This second type of coupling is controlled by $n^2$ in Eq. (7). Here, n represents the previously discussed effective transformer turns ratio between the source feed line (e.g., coaxial cable 7 or microstrip line 16) and the equivalent parallel $R_oLC$ network representing the microstrip resonator in FIGS. 2-7 or resonant slot 15 in FIG. 8. In FIGS. 2-7, the most effective way for adjustment of n is to symmetrically lengthen or shorten short slot 13 so that $r_o$ lies within a prescribed window. In FIG. 8, since the length of slot 15 is fixed according to the desired resonant frequency, n can be adjusted by displacing the coaxial feed line 7 by distance d from the center and along the axis of slot 15. With proper positioning, the impedance of slot 15 at resonance can be nearly matched to the characteristic resistance of coaxial feed line 7, and thereby achieve near-critical coupling.

There are applications of the invention where the complex dielectric properties of a test material are desired at several discrete microwave frequencies. This can be accomplished using a plurality of microstrip resonators as depicted in FIG. 7. In this embodiment three dipole resonators 11a, b, and c are all fed from a common electrically short slot feed 13. Each of the resonator lengths $L_a$, $L_b$ and $L_c$ are cut to give the desired resonant frequencies. Linear and logarithmic distributions in resonant frequencies are two convenient choices, i.e., $$f_n = f_1 + (n-1)\delta f \tag{14}$$

or $$f_n = f_1(f_N/f_1)^{n/N} \tag{15}$$

respectively, where n = 1, 2, ..., N. Here, $f_1$ and $f_N$ are the lowest and highest resonant frequencies respectively, $f_n$ is that of the nth resonator, and $\delta f$ is the uniform spacing interval between resonant frequencies in the linear distribution case.

Dipole resonators are preferred for the configuration depicted in FIG. 7 because several resonators can be closely spaced and driven from a common short feed slot 13. The use of eight such dipoles, spaced as close as 0.050 inch apart has been demonstrated. Because of the wide separation between the fundamental and third resonant frequencies for a dipole, the distribution of the N-resonant frequencies is typically taken to lie between $f_1$ and $3f_1$. The second resonance of a given dipole is not excited if the dipole 11 is fed at the center of its length by short slot 13. Also, the self-resonant frequency of the short slot feed 13 should be somewhat greater than $3f_1$. The dipoles are typically configured with the longest being centered about the feed slot 13, and successively shorter dipoles alternating on either side. This is because the longer and hence lowest frequency dipoles are best excited near the middle of the feed slot 13.

Conclusion and Scope of Invention

The several microstrip resonator embodiments of this invention provide low cost, rugged, highly sensitive and highly accurate sensors for measuring or monitoring the in situ complex dielectric and conductive properties of materials in all forms: solids, liquids, and gasses.

While the above descriptions of the different embodiments contain many specificities, these should not be construed as limitations on the scope of the invention. Rather, they are an exemplifications of preferred embodiments. Many other variations and applications are possible.

It should be apparent that the several embodiments to the basic invention are not dependent on each other, i.e., any one embodiment can be used without the need for one or more of the others. In particular, the basic embodiment in FIG. 2 can be used without any of the additional embodiments. These additional embodiments include:

a) Use of various other shapes of metal resonators, besides dipoles 11 or loop 25.
b) Use of various types of feed arrangements, besides the coaxial cable 7, microstrip line 16, or the short feed slot 13.
c) Use of shield 24 enclosing the short feed slot 13 as depicted in FIG. 4.
d) Use of a dielectric superstrate 26 as depicted in FIG. 6.
e) Use of multiple resonators 11a, b, c, as depicted in FIG. 7.

Similarly, sensor 60 in FIG. 8 may have additional or fewer parts, such as:

a) Elimination of substrate 12
b) Addition of a shield enclosing the feed slot 15 as in FIG. 4 to shield against radiation from the rear of the sensor.
c) The use of feed arrangements other than the coaxial cable 7, such as a coplanar stripline, microstripline, etc.

There may be other embodiments which can be made but which do not alter the basic concepts of the invention.

Although all of the sensors depicted in FIGS. 2–8 are shown having a smooth, flat face, this is not necessary. In many applications, particularly referring to solids having curved surfaces and to liquids, powders and gasses confined by curved containers or flow pipes, the sensor surface can be curved. For example, the sensor can be conformally mounted in a curved wall of such a container or pipe.

Further, although the sensors in FIGS. 2–4 and 6–8 are depicted as having rectangular shapes, this too is not necessary. Other shapes such as circular (FIG. 5), elliptical, etc. can also be used for particular applications and ease of fabrication.

The effective penetration depth of the electromagnetic fields into the test material, which is about half the resonator length (L/2), becomes important when considering application to test materials having finite depth, such as thin sheets, and to nonhomogeneous materials. As applied to sheets of material, if the sensor is designed to operate at low microwave frequencies, the electromagnetic fields may penetrate through the test material and into the medium beyond. This, in turn, causes $f_r$ to be different than it would be for an infinitely thick test material 9. In fact, this can be put to good advantage because the resulting $f_r$ is then an indicator of the electrical thickness of the test material 9. For example, if the medium beyond the sheet of test material is air, the fields which penetrate through the sheet and into the air beyond will cause $f_r$ to be higher than if the medium were infinitely thick. Conversely, if the material beyond the sheet is metal, this would cause $f_r$ to be lower than for a very thick test medium 9. A particular application where this feature is useful relates to measuring the thickness and complex dielectric constant of electronic substrate materials, either unclad or clad by metal on the side opposite to the sensor.

As applied to nonhomogeneous test materials, (i.e., those having varying degrees of porosity, moisture, voids, cracks, seams, and other anomalous features embedded within the sensing depth of the microstrip resonator) the resonant frequency $f_r$ is determined by the effective bulk real dielectric constant of the test material, $\epsilon'_{eff}$. If the real dielectric constant of the embedded anomalous material is less than that of the homogeneous material, then $\epsilon'_{eff}$ is less than $\epsilon'$. This happens, for example, when the anomalous material is contains gas bubbles (porosity). As a result, $f_r$ for a porous material will be higher than that for a homogeneous test material. Similar effects on $f_r$ are noted for embedded voids and cracks. Conversely, if the anomalous material has a larger dielectric constant than that of the homogeneous material, then $\epsilon'_{eff}$ is greater than $\epsilon'$, with a resulting reduction in $f_r$. This occurs, for example, when the anomalous material is moisture because water is highly polarizable to the microwave field and has an unusually large dielectric constant as noted previously.

In effect, the sensor is able to discern both positive and negative variations in the local average dielectric constant, $\epsilon'_{eff}$. This is done in real time by measuring $f_r$ as the test material passes by the sensor, or as the test material undergoes a transition as in curing, or as the sensor is scanned over the surface of a stationary solid material. While a real-time display of $f_r$ itself is very useful information, proper calibration of the sensor can be achieved to yield $\epsilon'_{eff}$ versus time or sensor position.

Calibration of the invention can be accomplished either empirically or analytically. In empirical calibration, $f_r$ is measured for several test materials having precisely known values of $\epsilon'$. Such solid materials can be purchased from several manufacturers of microwave dielectric materials. When the intended use pertains to solids, "standard" solids should be used for empirical calibration. Similarly, if the application pertains to liquids, calibration should be done using "standard" liquids. The most accurate empirical calibration is achieved using liquids, because close physical contact of the liquid with the microstrip resonator is automatically achieved when the sensor face is immersed into the liquid.

Analytical calibration is best accomplished by modeling the sensor configuration as in actual application, using numerical methods such as method of moments or finite difference computer codes.

The microstrip resonators shown in FIGS. 2–4, 6 and 7 all have the shape of thin dipoles having length L. While this particular shape has been shown to have many advantages relative to other shapes, e.g., rectangles, circular or elliptical rings or discs, triangles, bow ties, etc., the invention is not restricted to such dipole shapes. Some advantages of dipole resonators, compared to other shapes are:

a) Simple construction
b) Symmetric feeding at the dipole center in FIGS. 2–4, 6 and 7 only couples to the odd resonance modes. Consequently, the next higher mode (3rd) is very widely separated from the usually desired fundamental mode.
c) The long and narrow shape permits measuring or monitoring directional dielectric properties of the test material, i.e., its anisotropy.

For these reasons, the dipole is the preferred shape for most applications of this invention.

Similarly, the short slot is fed by a coaxial cable 7 in FIGS. 2, 3A, 4–7 but this invention is not restricted to such a feed arrangement. Several slot feed arrangements can be used, such as those described by Cohn U.S. Pat. No. 3,760,304), Fikart U.S. Pat. No. 4,123,730) or by Posar and Colleagues (Electronics Letters, 21(2), Jan. 17, 1985, pp. 49–50; Electronics Letters, 22(3), Jan. 30, 1986, pp. 125–126; IEEE Antennas and Propagation Society Newsletter, October 1986, pp. 5–9; IEEE Trans. On Antennas and Propagation, AP-35(6), June 1987, pp. 728–731) for application in the design and operation of microwave microstrip antennas. Such additional feed arrangements include feeding the slot 13 by means of a microstrip feed line extending normally from ground plane 14. Another method is to feed the slots 13 or 15 by means of an impedance transformer such as a tapered section of microstripline 16 or stripline. Another arrangement feeds the slots 13 or 15 by means of proximity coupling to an open-ended microstrip feed line as depicted in FIG. 3C. A short-circuited microstrip feedline can also be used, with a corresponding adjustment of length $L_{stub}$. Still another method, which does not use a slot, is to extend the center conductor 21 of the coaxial cable 7 through the substrate material 12 by means of a hole in the ground plane 14 and directly connecting it to the resonator 11 on the face of the sensor.

Important advantages of the slot feed arrangement, compared to other methods are:

a) The dimensions of the short slot 13 are easily trimmed to yield near-critical coupling and extremely sharp resonances as the source frequency is swept. This permits measurement of $f_r$ (and hence of $\epsilon'$ or $\sigma$ of test material 9), with the greatest accuracy and resolution.

b) The short slot 13 inductively couples to the resonator 11 in a noncontacting and perfectly balanced manner without need for a feed balun.

c) The coaxial feed line 7 or microstrip line 16 can exit from the slots 13 or 15 by passing along the ground plane 14, thereby maintaining a thin and flat profile.

For these reasons, the slot feed arrangement is the preferred type for most applications of this invention.

It would be apparent to someone familiar with microwave microstrip antennas that the microstrip sensors depicted in FIGS. 2–8 are similar to microstrip antennas in general form. But it would also be apparent that they are designed for quite different application, function and use. For example, microstrip antennas are designed to achieve prescribed far-field radiation pattern shapes over broad bandwidths (several percent). In contrast, microstrip resonator sensors are designed to achieve particular interactions with test material 9 in the near field (far field patterns are of no concern) and the sensors must have a very sharp resonance. Here, particular interactions of interest are the effective depth of field penetration, the desired sensitivities and the ability of the sensor to distinguish directional dielectric properties (i.e., anisotropy) of test material 9 placed in the near or reactive field. In contrast, microstrip antennas are designed as radiating devices for communications or surveillance purposes.

By scanning the sensor laterally (i.e., with x and y, where z is normal to the surface) over the surface of a solid, relief maps of $f_r$ and $r_o$ (or of $\epsilon'$, $\epsilon''$ or $\sigma$) versus the lateral surface coordinates can be generated. The detailed structure of such relief maps will show hills, peaks, valleys, ridges, etc., which are indicative of local anomalies, either on the surface or embedded within the depth of penetration.

The real dielectric constants of many microwave substrate 12 and superstrate 26 dielectric materials (e.g., PTFE/Glass) have a significant temperature dependence. This causes $f_r$ to change with temperature, everything else being constant. It is therefore good practice to choose dielectric substrate 12 and superstrate 26 materials having a small temperature dependence. For example, the dielectric constant of RT/duroid 6002 (manufactured by Rogers Corp., 100 S. Roosevelt Avenue, Chandler, Ariz. 85226) has a near zero temperature coefficient.

Accordingly, the scope of the invention should be determined not by the embodiments illustrated but by the appended claims and their legal equivalents.

I claim:

1. A microwave reflection sensor for measuring the in situ dielectric and conductive properties of a material, comprising:

a metal ground plane;

a dielectric substrate mounted on one surface (front) of the ground plane;

a highly conducting microwave resonator formed on the opposed surface of the substrate opposite the ground plane;

an electrically short feed slot formed in the ground plane and inductively coupled to the resonator;

an electrical feed means operatively connected to the slot for coupling microwave power to and receiving microwave power reflected from the slot, said feed means having an input coupling factor $r_o$ in the range $0.5 < r_o < 2.0$ at the resonant frequency of the resonator.

2. The reflection sensor of claim 1 wherein the microwave resonator is a metal dipole, and the electrically short feed slot is oriented substantially perpendicular to the dipole resonator.

3. The reflection sensor of claim 1 wherein the microwave resonator is a metal loop and the axis of electrically short feed slot is oriented substantially perpendicular to the loop circumference.

4. The reflection sensor of claim 1 further comprising a swept microwave frequency source connected to the electrical feed means, means for detecting a wave which is reflected from the short feed slot, and means to determine the resonant frequency of the resonator and the sensor input coupling factor at the resonant frequency of the resonator.

5. The reflection sensor of claim 1 wherein the electrical feed means comprises a coaxial cable connected across the feed slot.

6. The reflection sensor of claim 1 wherein the electrical feed means comprises a microstrip line connected across the slot and oriented substantially perpendicular to the slot axis.

7. the reflection sensor of claim 1 wherein the electrical feed means comprises a microstrip line which extends over and across the short slot substantially perpendicular to the slot axis and is terminated in an open or short circuit so that the standing wave on the microstrip line couples to the slot.

8. The reflection sensor of claim 1 wherein the sensor is substantially flat.

9. The reflection sensor of claim 1 wherein the sensor conforms to the shape of a material to be measured or to the shape of a vessel containing the material to be measured.

10. The reflection sensor of claim 1 further comprising a metallic shield formed around the short feed slot on the back side of the ground plane to prevent radiation from the back side of the sensor.

11. The reflection sensor of claim 1 further comprising a dielectric superstrate formed on the resonator and the opposed surface of the dielectric substrate to diminish the electromagnetic coupling between the resonator and the material to be measured, and to protect the resonator from damage and wear.

12. The reflection sensor of claim 1 further comprising a plurality of additional microwave resonators formed on the opposed surface of the substrate, each resonator having a different resonant frequency.

13. The reflection sensor of claim 12 wherein the resonators are parallel dipoles of different lengths.

14. A microwave reflection sensor for measuring the in situ dielectric and conductive properties of a material, comprising:
a metal ground plane;
a dielectric substrate mounted on one surface (front) of the ground plane;
one or more highly conducting resonators formed on the opposed surface of the substrate opposite to the ground plane; single electrical feed means operatively connected to the sensor for coupling incident microwave power to and for receiving microwave power reflected from the one or more resonators such that the coupling factor $r_o$ at the sensor feed connection is within the range $0.5 < r_o < 2.0$ at one or more resonant frequencies of the one or more resonators.

15. The reflection sensor of claim 14 further comprising a dielectric superstrate formed on the one or more resonators and the opposed surface of the dielectric substrate to diminish the electromagnetic coupling between the one or more resonators and the material being measured, and to protect the one or more resonators from damage and wear.

16. The reflection sensor of claim 14 wherein the feed means comprises an electrically short slot in the ground plane, oriented to inductively couple to the one or more resonators and electrically fed by connecting a coaxial cable across the slot.

17. The reflection sensor of claim 14 wherein the feed means comprises an electrically short slot in the ground plane, oriented to inductively couple to the one or more resonators and fed by a microstrip line which is either conductively connected across the slot or extends across and beyond the slot at essentially a right angle to the slot axis and is terminated in an open or short circuit so that a standing wave on the microstrip line couples to the slot.

18. The reflection sensor of claim 17 wherein the microstrip feed line is formed on a second dielectric substrate which is mounted on the back side of the ground plane.

19. The reflection sensor of claim 14 wherein the feed means comprises an electrically short slot in the ground plane, oriented to inductively couple to the one or more resonators and fed by a coplanar line formed in the ground plane, the coplanar line being substantially perpendicular to the slot axis and having its center conductor conductively connected across the slot.

20. The reflection sensor of claim 14 further comprising a swept microwave frequency source connected to the electrical feed means, means for detecting a wave reflected from the feed means, and means for measuring the resonant frequencies and the sensor input coupling factors at the resonant frequencies of the one or more resonators.

21. A microwave reflection sensor for measuring the in situ dielectric and conductive properties of a material, comprising:
a metal ground plane;
a narrow resonant slot formed in the ground plane;
electrical feed means operatively connected to the slot for coupling a microwave source electromagnetically to the slot such that the coupling factor $r_o$ between the source and the slot is within the range $0.5 < r_o < 2.0$ at the resonant frequency of the slot.

22. A reflection sensor of claim 21 in which the ground plane and slot are covered with a dielectric substrate on the side opposite (front) to the electrical feed means.

23. The reflection sensor of claim 21 in which the electrical feed means is a coaxial cable connected across the slot at some offset distance from the center of the slot length.

24. The reflection sensor of claim 21 in which the electrical feed means comprises a microstrip line which is either conductively connected across the slot at some offset distance from the center of the slot length, or extends some distance beyond the slot at substantially a right angle to the slot axis and is terminated in an open or short circuit so that a standing wave on the microstrip line couples to the slot.

25. The reflection sensor of claim 21 in which the electrical feed means is a coplanar transmission line formed in the ground plane, the coplanar line being oriented substantially perpendicular to the slot axis and having its center conductor connected across the slot at some offset distance from the center of the slot length.

26. The reflection sensor of claim 21 further comprising a swept microwave frequency source connected to the electrical feed means, means for detecting a wave reflected from the feed means, and means for measuring the resonant frequency of the slot and the sensor input coupling factor at the resonant frequency of the slot.

27. A method for measuring the in situ dielectric and conductive properties of a material, comprising:
forming a narrow resonant slot in a ground plane;
coupling a microwave source electromagnetically to the slot with a coupling factor $r_o$ between the source and the slot in the range $0.5 < r_o < 2.0$ at the resonant frequency of the slot;
contacting the ground plane and slot with the material;
detecting a reflected wave from the slot;
measuring the resonant frequency of the slot and the input coupling factor at the resonant frequency of the slot.

28. A method for measuring the in situ dielectric and conductive properties of a material, comprising:
forming a highly conducting microwave resonator on a dielectric substrate mounted on a metal ground plane;
coupling a microwave source electromagnetically to the resonator with a coupling factor between the source and the resonator in the range $0.5 < r_o < 2.0$ at the resonant frequency of the resonator;
contacting the dielectric substrate and resonator with the material;
detecting a reflected wave from the resonator;

measuring the resonant frequency of the resonator and the input coupling factor at the resonant frequency of the resonator.

29. A microwave reflection sensor for measuring the in situ dielectric and conductive properties of a material, comprising:

a metal ground plane;

a dielectric substrate mounted on one surface (front) of the ground plane;

one or more highly conducting parallel dipole resonators formed on the opposed surface of the substrate opposite to the ground plane;

an electrically short slot formed in the ground plane, said slot being inductively coupled and oriented substantially perpendicular to all of the one or more parallel dipole resonators;

a coaxial cable connected across the slot to feed the slot with an input coupling factor $r_o$ in the range $0.5 < r_o < 2.0$ at one or more of the resonant frequencies of any of the one or more resonators.

* * * * *